United States Patent [19]

Saotome et al.

[11] Patent Number: 4,624,909

[45] Date of Patent: Nov. 25, 1986

[54] SILICON-CONTAINING NOVOLAK RESIN AND RESIST MATERIAL AND PATTERN FORMING METHOD USING SAME

[75] Inventors: Yasushi Saotome; Hiroshi Gokan; Kazuhide Saigo; Masayoshi Suzuki; Yoshitake Ohnishi, all of Tokyo, Japan

[73] Assignee: NEC Corporation, Tokyo, Japan

[21] Appl. No.: 724,457

[22] Filed: Apr. 18, 1985

[30] Foreign Application Priority Data

Apr. 27, 1984 [JP] Japan .................................. 59-85231
Sep. 27, 1984 [JP] Japan ................................. 59-202323
Sep. 28, 1984 [JP] Japan ................................. 59-203222
Oct. 1, 1984 [JP] Japan ................................. 59-205928

[51] Int. Cl.$^4$ .................... C08G 77/00; C08G 8/28; C08G 77/60
[52] U.S. Cl. ................................. 430/192; 430/106; 430/190; 430/191; 430/314; 430/323; 430/905; 528/25; 422/62; 422/148
[58] Field of Search ................... 528/25; 430/106, 190, 430/191, 192, 314, 323, 905; 422/42, 148

[56] References Cited

U.S. PATENT DOCUMENTS

| | | | |
|---|---|---|---|
| 2,182,208 | 12/1939 | Nason | 528/25 X |
| 2,611,776 | 9/1952 | Speier, Jr. | 528/25 X |
| 2,611,777 | 9/1952 | Speier, Jr. | 528/25 X |
| 2,611,780 | 9/1952 | Speier, Jr. | 528/25 X |
| 2,645,630 | 7/1953 | Speier, Jr. | 528/25 X |
| 3,074,903 | 1/1963 | Fincke et al. | 525/480 |
| 3,081,269 | 3/1963 | Shannon et al. | 525/480 X |
| 3,137,720 | 6/1964 | Cooper | 528/25 X |
| 3,234,159 | 2/1966 | Cooper | 525/504 X |
| 3,481,901 | 12/1969 | Prochaska | 525/480 |
| 3,847,860 | 11/1974 | Seiler et al. | 525/504 X |
| 4,022,753 | 5/1977 | Lohse et al. | 525/480 |
| 4,032,511 | 6/1977 | Blount | 528/25 X |
| 4,043,929 | 8/1977 | Gibson et al. | 430/904 X |
| 4,045,397 | 8/1977 | Parkinson | 525/480 X |
| 4,070,296 | 1/1978 | Gibson et al. | 430/106 |
| 4,094,825 | 6/1978 | Blount | 528/25 X |
| 4,529,682 | 7/1985 | Toukhy | 528/162 X |
| 4,587,205 | 5/1986 | Harrah et al. | 528/25 X |

FOREIGN PATENT DOCUMENTS 0096596 12/1983 European Pat. Off. .

OTHER PUBLICATIONS

J. Electrochemical Soc. 130(1983), 1962-1964, Suzuki et al.

*Primary Examiner*—Howard E. Schain
*Attorney, Agent, or Firm*—Burns, Doane, Swecker & Mathis

[57] ABSTRACT

Disclosed is a novel novolak resin comprising structural units having a trimethylsilyl group. A resist material highly resistive to dry etching is obtained by adding a photosensitive diazo compound to this novolak resin. The resist material is useful in various lithography methods to form a positive resist pattern. This resist material is used in a pattern forming method of a two-layer type, in which a fine pattern is formed in a thin film of the resist material by lithography and then transferred into an underlying thick organic polymer layer by dry etching of the underlying layer with the resist pattern as mask. Curing of the resist pattern by irradiation with deep UV rays is effective for further improvement in the precision of the transferred pattern.

34 Claims, No Drawings

SILICON-CONTAINING NOVOLAK RESIN AND RESIST MATERIAL AND PATTERN FORMING METHOD USING SAME

BACKGROUND OF THE INVENTION

This invention relates to a novel novolak resin containing silicon and a resist material which comprises the novolak resin and is useful in forming fine patterns in the manufacture of microelectronic devices, and to a pattern forming method in which the novel resist material is used to form a resist pattern that servies as a mask for dry etching of an underlying organic layer.

In the manufacture of microelectronic devices such as semiconductor integrated circuit devices and bubble memory devices, optical lithography and electron-beam lithography are widely used to from fine patterns. In such techniques the thickness of a resist layer is an important factor in realization of high resolution patterns. It is well known that the use of a thick resist layer results in low resolution mainly by reason of reflection from the substrate in the case of optical lithography and scattering of electrons in the case of electron-beam lithography. However, when the resist layer is made thin to thereby obtain a high resolution pattern there arises a problem that in the subsequent etching process the resistivity of the resist pattern is insufficient. This is particularly serious when a dry etching technique such as reactive ion etching or ion beam etching is employed in the subsequent process since conventional resist materials are generally low in resistivity to dry etching.

Besides, it is not seldom that the surface of the substrate has steps, and in such cases it is difficult to form fine patterns by a conventional lithography method even if the overlying resist layer is made fairly thin.

To solve the above described problems, J. M. Moran et al have proposed a three-layer technique in J. Vacuum Science and Technology, 16, No. 6, 1620 (1979). Accordingly to this three-layer technique the first layer which covers the substrate surface and provides a flat surface is a sufficiently thick layer of an organic material, and the intermediate layer is formed of an inorganic material that can not easily be etched by dry etching with oxygen, such as silicon, silicon dioxide or silicon nitride. The third or top layer is a thin resist layer. In the patterning process, first the resist layer is exposed to light, X-ray or electron-beams and developed to produce a resist pattern. Next, the intermediate layer is subjected to etching with the resist pattern as a mask. Finally the thick organic layer is etched by reactive sputter etching using oxygen with the patterned intermediate layer as a mask. By this method a high resolution pattern initially delineated in the thin resist layer can be transferred to the organic layer. However, it is a disadvantage of the three-layer method that the processing operations become complicated and time-consuming mainly because of the addition of the intermediate layer which is formed by vacuum deposition, sputtering or plasma CVD method.

If it is practicable to use a resist material which is sufficiently resistive to dry etching the above described three-layer structure can be simplified to a two-layer structure. However, conventional resist materials do not meet this desire. Polydimethylsiloxane is known as resistive to dry etching, but this polymer is unsuitable for practical use as a resist material because it is liquid at room temperature.

As a practical solution of the above problems, J. Electrochem. Soc., 130, 1962 (1983) and European patent application publication No. 0096596 have disclosed a pattern forming method of a two-layer type using a new resist material which comprises a polymer having trialkylsilyl groups or dimethylphenylsilyl groups. This resist material is highly resistive to reactive oxygen ion etching and is sensitive to electron beams and deep UV rays, and the simple two-layer structure consisting of a relatively thick organic layer laid on a substrate and a thin resist layer is favorable for industrial practice. Howevr, this pattern forming method is practicable only when the resist pattern is a positive pattern.

SUMMARY OF THE INVENTION

It is an object of the present invention to provide a novel novolak resin which is useful as a basic material of a resist material resistive to dry etching.

It is another object of the invention to provide a novel resist material which is highly resistive to dry etching and is useful in forming fine positive resist patterns with high resolution.

It is still another object of the invention to provide a method of forming fine patterns in the manufacture of microelectronic devices by using a dry etching technique and a resist material according to the invention.

First, this invention provides a novolak resin comprising structural units having a trimethylsilyl group attached to benzene ring of a phenol via at least one methylene group.

More specifically, the novel novolak resin comprises either structural units represented by the general formula (A) or structural units represented by the general formula (B).

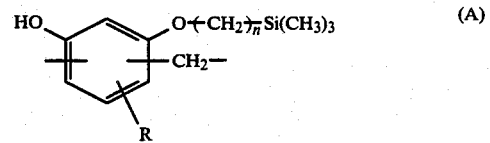

wherein R represents hydrogen atom or an alkyl group, and n is a positive integer.

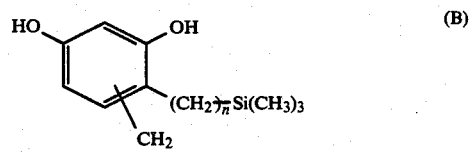

wherein n is a positive integer.

In the case of the structural units represented by the general formula (A), it is preferable that the structural units are represented by the general formula (AA):

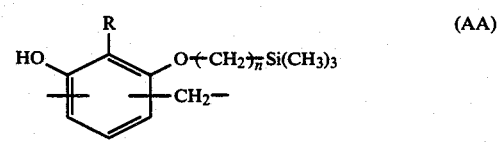

wherein R represents hydrogen atom or methyl group, and is an integer of 1 to 3.

A novolak resin according to the invention may optionally comprise secondary structural units represented by the formula (C) together with the primary structural units or the general formula (A) or (B).

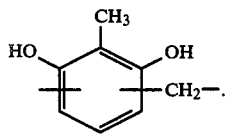
(C)

Furthermore, the present invention provides a resist material which comprises a novolak resin comrising structural unit having a trimethylsilyl group attached to benzene ring of the phenol via at least one methylene group and a photosensitive diazo compound.

In this resist material the particulars of the structural units of the novolak resin are as stated above. As the photosensitive diazo compound, usually a quinonediazo compound is preferable. Where it is intended to form a resist pattern by exposure to deep UV rays, it is advantageous to use a diazo compound represented by the general formula (D), viz. 2,2-(2-substituted)-5-diazo-1,3-dioxane-4,6-dione, as the photosensitive material.

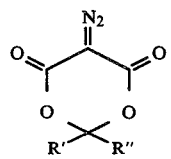
(D)

wherein each of R′ and R″ represents a substituted or unsubstituted alkyl group or a substituted or unsubstituted aryl group, and R′ and R″ may be either identical or different.

A resist material according to the invention can be made sensitive to electron beams, X-rays, UV rays, deep UV rays and/or visible light and provides a film highly resistive to dry etching such as oxygen ion beam etching or reactive ion etching using either oxygen or nitrogen-hydrogen. A very thin resist layer formed by applying this resist material can serve as a mask for etching an underlying thick organic layer by dry etching. For example, when etching a conventional novolak resin or polyimide resin layer as thick as about 15000 Angstrom, it suffices that the resist layer has a thickness of about 2000 Angstrom. By using this resist material, a positive resist pattern can easily be formed by a conventional exposure method.

In another aspect, the present invention provides a pattern forming method of a two-layer type, which comprises the steps of forming an organic polymer layer, which can be etched by dry etching, on a substrate to be ultimately processed, forming a resist film on the organic polymer layer by applying a resist material according to the present invention, forming a desired pattern in the resist film by a lithography technique, and etching the organic polymer layer by a dry etching technique with the patterned resist film as a mask.

By using this pattern forming method, a fine pattern, which may be a submicron pattern, formed in a very thin resist film can accurately be transferred into the underlying thick organic polymer layer by a dry etching method. Since the resist film thickness can be reduced it has become easy to obtain high resolution patterns. Owing to the existence of a relatively thick organic polymer layer beneath the resist film, the unfavorable effect of reflection from the substrate and the abnormal proximity effect over the stepped areas of the substrate are eliminated in the initial etching process for forming the resist pattern. Furthermore, this pattern forming method requires less operation steps than a pattern forming method using the above described three-layer structure. In the present invention, optical lithography can be used for forming a positive resist pattern.

DESCRIPTION OF THE PREFERRED EMBODIMENTS

The primary features of a novolak resin according to the invention are as described hereinbefore. Usually the degree of polymerization of this novolak resin does not exceed 20 in terms of the number of the structural units of the general formula (A) or (B). In the case of the structural units of the general formula (B), it is desirable that n in (B) is smaller than 4 in view of both the content of Si in the resin and solubility of the resin.

It is permissible that the novolak rsin comrises secondary structural units represented by one of the following formulas (E), (F) and (G) in place of the aforementioned secondary structural units of the formula (C). However, structural units of the formula (C) are best as secondary structural units from the viewpoint of increasing the alkali solubility of the novolak resin.

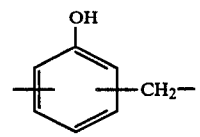
(E)

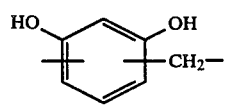
(F)

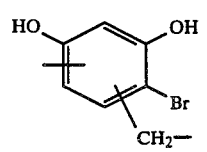
(G)

For use in a resist material, a novolak resin according to the invention needs to be soluble in at least one kind of practicable solvent since the resist material is usually applied in the form of solution. Besides, the novolak resin needs to be soluble in a liquid useful for the development purpose, such as an aqueous solution of an alkaline compound. For these reasons it is desirable that the content of the primary structural units of the general formula (A) or (B) in the novolak resin is not more than 80% by mol. On the other hand, it is desirable that the content of the structural units of the general formula (A) or (B) in the novolak resin is not less than 20 mol% with a view to realizing sufficient resistivity to dry etching.

In preparing a resist material by the addition of a photosensitive material to a novolak resin according to the invention, the photosensitive material can be selected from various diazo compounds that are initially insoluble in an aqueous alkali solution and transform into another state soluble in the same solution when irradiated with electron beams, ion beams, X-rays, UV rays, deep UV rays or visible light. Considering the sensitivity to optical irradiation, it is desirable to make a selection from quinonedizide compounds. These compounds are sensitive to electron beams ion beams, X-rays and deep UV rays too.

Particularly suitable quinonediazide compounds are ones formed by condensation reaction between a low molecular or high molecular compound having either a naphthoquinonediazide group or a benzoquinonediazide group, such as naphthoquinonediazide sulfochloride or benzoquinonediazide suflochloride, and a low molecular or high molecular compound having a hydroxyl group. For example, the low molecular comound having a hydroxyl group may be hydroquinone, resorcinol, phloroglucinol, 2,4-dihydroxybenzophenone or 2,3,4-trihydroxybenzophenone, and the high molecular compound having a hydroxyl group may be a phenolic resin or polyhydroxystyrene.

In the resist material, it is suitable that the amount of the photosensitive material is 5 to 100 parts by weight, and preferably 15 to 50 parts by weight, per 100 parts by weight of the novolak resin. Besides the photosensitive material, some auxiliary additives may optionally be added. Examples of auxiliary additives are additional resins to improve the adhesion of the resist film to the underlying organic polymer layer, plasticizers, pigments and/or dyes which serve as light absorbing agents.

To obtain a resist material highly sensitive to deep UV rays, it is particularly suitable to use a diazo compound represented by the general formula (D) as the photosensitive material. Also in this case, a suitable range of the proportion of the diazo compound to the novolak resin is from 5:100 to 100:100 by weight. In this case, a preferable range is from 20:100 to 50:100 by weight, and it is preferred that the primary structural units of the novolak resin are of the formula (AA) or of the formula (B).

An experiment on the use of compounds of the general formula (D) as the photosensitive material in a positive resist for deep UV exposure is reported in IEEE Transactions on Electron Devices, 28, 1300 (1981), but the results were unsatisfactory in the resolution and precision of the patterns and also in reproducibility. However, when similar compounds of the general formula (D) are used in combination with a novolak resin according to the present invention fine patterns of 0.5 micrometers linewidth can be formed by deep UV exposure with high precision and with good reproducibility. In the present invention the compounds of the general formula (D) can be used also when the resist material is to be irradiated with electron beams, ion beams or X-rays.

In the pattern forming method according to the invention, first the substrate surface is coated with a sufficiently thick layer of an organic polymer such as a conventional novolak resin. After solidification of the organic polymer layer a solution of a resist material according to the invention is applied usually by spinning. For example, the solvent for preparing the resist material solution is xylene, isoamyl, ehtyl cellosolve acetate, methyl cellosolve acetate or cellosolve acetate, or a mixture of two or three of the named solvents. Of course it is necessary to select a solvent that does not dissolve or swell the firstly formed organic polymer layer. The applied solution is dried by heating under appropriate conditions to thereby complete a resist film. Then a desired pattern is delineated in the resist film by irradiation with electron beams, ion beams, X-rays, UV rays, deep UV rays or visible light using a patterned mask, and the desired resist pattern is obtained by performing development. In this method, any aqueous alkaline solution can be used as the developer liquid. For example, the solute of such a solution may be either an inorganic base such as sodium hydroxide or potassium hydroxide or an organic base such as choline or tetramethylammonium hydroxide. Besides an alkaline substance, the developer liquid may optionally contain a surface-active agent and/or any other auxiliary additive.

Using the resist pattern obtained by the above described process as a mask, the underlying thick layer of the organic polymer is etched by a dry etching method represented by a reactive ion etching method using oxygen or an oxygen ion beam etching method to thereby transfer the fine resist pattern into the thick organic polymer layer.

In the above described pattern forming method, it is advantageous and preferable to cure the resist pattern after development by intense irradiation with deep UV rays over the entire areas. The light source is not limited insofar as the wavelength are in the range from about 2000 Angstrom to about 3000 Angstrom. It is suitable that the dose of irradiation amounts to 0.1–10 J/cm$^2$. In the case of curing the resist pattern in this manner, it is preferable that the novolak resin in the resist material comprises structural units of the general formula (AA) or of the general formula (B).

With respect to an organic resit not containing Si or any other metal, it has already been tried to prevent deformation of the resist pattern by curing the resist pattern by irradiation with deep UV rays, as reported in J. Electrochem. Soc., 128, 2645 (1981). However, curing of such an organic resist film does not produce an appreciable improvement in the resistivity to dry etching by oxygen. In contrast, a resist film using a Si-containing novolak resin of the invention exhibits remarkable enhancement of resistivity to dry etching by oxygen or an alternative gas when cured by irradiation with deep UV rays. Accordingly, the addition of the resist pattern curing step before etching the underlying thick organic polymer layer is very effective for accurate transfer of the resist pattern into the organic polymer layer. By doing the curing, the pattern transferring etching can be accomplished with less errors in the shape of the pattern, and the dimensional precision of the transferred pattern is improved. Since the cured resist pattern is very highly resistant to dry etching such as reactive ion etching using either oxygen or nitrogen-hydrogen or oxygen ion beam etching, a resist film thickness of about 1500 Angstrom is sufficient for the masking purpose in dry etching of an organic polymer layer as thick as about 15000 Angstrom.

The invention will further be illustrated by the following nonlimitative examples.

EXAMPLE 1

1. Synthesis of Monomer

In a 200 ml flask to which a dropping funnel and a reflux condenser were connected, 4.6 g of metallic sodium was dissolved in 100 ml of ethanol by stirring with magnetic stirrer until a homogeneous solution was obtained. Then 22 g of resorcinol was added, and stirring was continued for 1 hr while reflux was continued. Next, still continuing reflux, 24.5 g of trimethylsilylchloromethane was dropped into the flask by the dropping funnel in 2 hr. After that reflux was continued for additional 24 hr. The reaction liquid was allowed to stand and cool down and the subjected to reduced pressure distillation for removal of ethanol. After adding 30 ml of water and a small amount of concentrated hydrochloric acid to create a weakly acidic condition, extraction of the reaction product with 30 ml of chloroform was repeated four times. The liquid extract was collected into a single vessel and washed with water four times each time using 30 ml of water. The washed chloroform solution was dehydrated with anhydrous magnesium sulfate and then subjected to distillation under reduced pressure to obtain 12.6 g of a distillate having a boiling point of 86° C. at 0.2 Torr. This distillate was confirmed to be 3-(trimethylsilylmethoxy)phenol, represented by the formula (1), from the following analytical results. This compound will be referred to as M-1.

Nuclear Magnetic Resonance (NMR) Spectrum Characteristics (in CDCl₃, δ, ppm): 0.1 (9H, s, 3CH₃), 3.5 (2H, s, CH₂), 5.0 (1H, s, OH), 6.0–7.3 (4H, m, Ar).

Infrared Absorption Characteristics (KBr disk, cm⁻¹): 3350 (OH), 1255 (SiCH₃).

Elementary Analysis: C 61.3%, H 8.3%

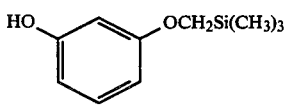

(1)

2. Preparation of Novolak Resin 5.0 g of monomer M-1, 2.1 g of 2-methylresorcinol and 3.7 g of 35% formalin were dissolved in 21 g of ethanol, followed by the addition of 10 drops of concentrated hydrochloric acid. The solution was kept heated at reflux temperature for 12 hr to thereby accomplish an addition-condensation reaction. After that the reaction liquid was poured into 500 ml of water to precipitate a polymer powder, which had a pale yellow color and weighed 7.6 g in dry state. This polymer was a novolak resin soluble in various organic solvents such as alcohols, acetone, chloroform and ethyl cellosolve acetate and also in aqueous alkaline solutions such as 1N aqueous solution of sodium hydroxide and 1N aqueous solution of tetramethylammonium hydroxide. This novolak resin is named P-1.

Using the same monomer M-1, five different novolak resins P-2, P-3, P-4, P-5, P-6 were prepared by varying the quantities of M-1, 2-methylresorcinol and 35% formalin in the above described addition-condensation reaction process as shown in Table 1.

TABLE 1

| Novolak Resin | Raw Materials | | | Yield of Resin (g) | Solubility in 1 N NaOH |
|---|---|---|---|---|---|
| | M-1 (g) | 2-methyl-resorcinol (g) | 35% formalin (g) | | |
| P-1 | 5.0 | 2.1 | 3.7 | 7.6 | soluble |
| P-2 | 5.0 | 3.2 | 4.2 | 8.5 | soluble |
| P-3 | 5.0 | 2.6 | 4.0 | 8.1 | soluble |
| P-4 | 5.0 | 1.7 | 3.1 | 7.0 | insoluble |
| P-5 | 5.0 | 1.2 | 2.8 | 6.5 | insoluble |
| P-6 | 7.0 | — | 2.9 | 7.3 | insoluble |

EXAMPLE 2

In the monomer synthesizing process of Example 1, the starting Si-containing compound was changed to synthesize a different monomer, which was confirmed to be 2-methyl-3-(trimethylsilylmethoxy)phenol represented by the formula (2). This compound (referred to as M-2) had a boiling point of 81° C. at 0.15 Torr and contained 62.8% of C and 8.8% of H by elementary analysis.

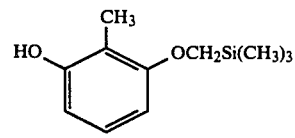

(2)

Using 5.0 g of monomer M-2, 3.0 g of 2-methyl resorcinol and 4.1 g of 35% formalin, the addition-condensation reaction described in Example 1 was similarly carried out. The reaction product was 8.6 g of a novolak resin in powder form, which was soluble in organic solvents and also in N aqueous solution of NaOH. The novolak resin is named P-7.

EXAMPLE 3

In the monomer synthesizing process of Example 1, the starting Si-containing compound was changed to synthesize another monomer, which was confirmed to be 3-(3-trimethylsilylpropoxy)phenol represented by the formula (3). This compound (referred to as M-3) has a boiling point of 117° C. at 0.1 Torr and contained 64.4% of C and 8.9% of H by elementary analysis.

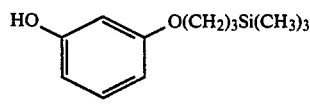

(3)

Using 5.0 g of monomer M-3, 6.5 g of 2-methylresorcinol and 6.4 g of 35% formalin, the addition-condensation reaction described in Example 1 was similarly carried out. The reaction product was 12.5 g of a novolak resin in powder form, which was soluble in organic solvents and also in 1N aqueous solution of NaOH. This novolak resin is named P-8.

EXAMPLE 4

A resist material solution RS-1 was prepared by dissolving 6.2 g of novolak resin P-1 prepared in Example 1 and 1.8 g of a photosensitive material Q-1, which was the product of condensation reaction between naphthoquinone-(1,2)-diazide-(2)-5-sulfochloride and p-cresol, in 62 g of ethyl cellosolve acetate, followed by filtration with a 0.2 micrometers filter.

Using the same novolak resin P-1, two different resist material solutions RS-2 and RS-3 were prepared by changing the photosensitive material and solvent as shown in Table 2. Besides, four different resist material solutions RS-4, RS-5, RS-6 and RS-7 were prepared by selectively using the novolak resin P-2 of Example 1, P-7 of Example 2 or P-8 of Example 3 in combination with a photosensitive material and solvent selected as shown in Table 2.

In Table 2, the symbols and abbreviations represent the following photosensitive materials and solvents, respectively.

Q-2: the product of condensation reaction between naphthoquinone-(1,2)-diazide-(2)-5-sulfochloride and 2,4-dihydroxybenzophenone.

Q-3: the product of condensation reaction between naphthoquinone-(1,2)-diazide-(2)-5-sulfochloride and 2,3,4-trihydroxybenzophenone.

EEA: ethyl cellosove acetate.

XY: xylene.
BA: butyl acetate.

TABLE 2

| Resist Material Solution | Novolak Resin | Photosensitive Material | Solvent |
|---|---|---|---|
| RS-1 | P-1 6.2 g | Q-1 1.8 g | EEA 62 g |
| RS-2 | P-1 6.0 g | Q-2 1.8 g | EEA 57 g |
| RS-3 | P-1 3.1 g | Q-3 1.4 g | EEA 20 g, XY 2 g, BA 2 g |
| RS-4 | P-2 3.1 g | Q-1 1.4 g | EEA 20 g, XY 2 g, BA 2 g |
| RS-5 | P-7 6.2 g | Q-1 2.5 g | EEA 50 g |
| RS-6 | P-7 6.0 g | Q-3 2.0 g | EEA 30 g, XY 3 g, BA 3 g |
| RS-7 | P-8 6.2 g | Q-1 2.7 g | EEA 40 g |

Among the resist material solutions shown in Table 2, RS-1 and RS-2 were used in the following experiment to evaluate the resistivity of novolak resin films according to the invention to dry etching.

The solution RS-1 was applied by spinning to a silicon substrate and dried at 80° C. for 30 min to thereby form a resist film 3500 Angstrom thick. The resist film was subjected to reactive oxygen ion etching. The etching operation conditions: oxygen flow rate was 5 sccm; oxygen pressure was 1.5 Pa; rf power was 100 W. In 6 min, the initial film thickness, 3500 Angstrom, reduced to 2500 Angstrom. By the same etching method and under the same etching conditions, a film of a conventional novolak resin (MP-1300 of Shipley Co.) was etched by about 12500 Angstrom in 6 min. Therefore, it was understood that a resist film formed by using RS-1 can be used as a mask for dry etching of a thick organic layer with oxygen ions.

By the same etching method and under the same etching conditions, a film formed by using the resist material solution RS-2 was etched by 1400 Angstrom in 6 min. Accordingly, a reist film formed by applying RS-2 too can be used as a mask for dry etching of a thick organic layer with oxygen ions.

Another experiment was conducted to evaluate resistivity of the above two kinds of resist films to dry etching by oxygen ion beam. The etching operation conditions: acceleration voltage was 100 V; ion current density was 0.25 mA/cm$^2$; oxygen pressure was 2.6 Pa. In 28 min, the thickness of the film formed by using the solution RS-1 decreased from the initial value 3500 Angstrom to 3000 Angstrom, and the thickness of the film formed by using RS-2 decreased from the initial value 3500 Angstrom to 2800 Angstrom. By the same etching method and under the same etching conditions, a film of MP-1300 was etched by about 12500 Angstrom. Therefore, either of the tested resist films can be used as a mask in a dry etching operation by oxygen ion beam.

In a separate experiment, a positive resist image produced by optical exposure in a film formed by applying the solution RS-1 was transferred into an underlying thick organic layer. First, MP-1300 was spun to a silicon substrate to a thickness of 10000 Angstrom, and prebaking was performed at 250° C. for 1 hr. Then, the solution RS-1 was spun onto the surface of the MP-1300 layer and dried at 80° C. for 30 min to thereby form a resist film 2000 Angstrom thick. A positive resist image was produced with submicron linewidth by the steps of placing a patterned chromium mask on the resist film, exposing the masked sample to light for 20 sec by using Kasper 2001P exposure apparatus equipped with a light source of 4000 Angstrom wavelength and making development with 0.8N aqueous solution of sodium hydroxide. After rinsing and drying, the MP-1300 layer beneath the resist image was etched by reactive oxygen ion etching for 6 min under the etching conditions mentioned in the first experiment. As the result, the submicron resist image was transferred into the underlying MP-1300 layer with good precision. This thick image or pattern obtained by the transfer of the positive resist image possessed a sufficient masking capability at the time of subsequent processing of the substrate, such as etching, ion implantation or lift-off. In an additional run of this experiment, an oxygen ion beam etching method was employed instead of the reactive oxygen ion etching method. Also in this case the transfer of the resist image into the MP-1300 layer was achieved with good precision. Furthermore, the resist material solutions RS-2, RS-3, RS-4, RS-5, RS-6 and RS-7 were tested in the same manner and gave nearly the same good results.

EXAMPLE 5

1. Preparation of Monomer

First, 2.5 g of 3-cyano-1-trimethylsilylpropane, 0.45 g of zinc chloride and 1.95 g of resorcinol were dissolved in 15 ml of anhydrous ehter. At 0° C. hydrogen chloride gas was blown into this solution for 1 hr, and the solution was left standing in a refrigerator for 24 hr. This procedure was repeated five times. After that the solution was left standing in a refrigerator for 1 week to allow growth of white crystals of a synthesized compound. The crystals separated from the mother liquor by filtration were put into 10 ml of water and heated at 100° C. for 3 hr. After cooling the crystals were refined by extraction with 30 ml of ether, followed by washing with 20 ml of water, which was repeated once more. Ether was completely evaporated to leave 2.6 g of a solid substance having a slightly yellowish white color. This solid substance was confirmed to be a compound represented by the formula (4), viz. 4-trimethylsilyl-1(2,4-dihydroxyphenyl)-1-butanone, from the following analytical results.

NMR Spectrum Characteristics (in CDCl$_3$, δ, ppm): 0 (9H, s, 3CH$_3$), 0.3–0.7 (2H, m, CH$_2$), 1.5–2.0 (2H, m, CH$_2$), 2.9 (2H, t, CH$_2$), 6.3–7.8 (5H, m, Ar+OH).

Infrared Absorption Characteristics (KBr disk, cm$^{-1}$): 3150 (OH), 1255 (SiCH$_3$).

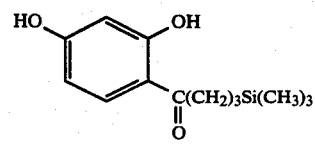

(4)

In a mixture of 10 ml of water and 3 ml of toluene, 1.6 g of the compound of the formula (4) was subjected to reduction by using zinc amalgam. After adding 10 ml of hydrochloric acid, the mixture was kept heated at reflux temperature for 24 hr. After natural cooling, an ether soluble component was extracted and washed with 30 ml of water twice. Ether was completely evaporated to leave 1.46 g of a solid compound, which was confirmed to have the structure of the formula (5) form the following NMR spectrum characteristics (in CDCl$_3$, δ, ppm): 0 (9H, s, 3CH$_3$), 0.3–0.7 (2H, m, CH$_2$), 1.0–1.8 (4H, m, 2CH$_2$), 2.5 (2H, t, CH$_2$), 5.5 (2H, br, 2OH), 6.2–7.0 (3H, m, Ar).

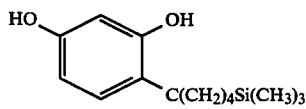

This compound will be referred to as M-4.

2. Preparation of Novolak Resin 1.0 g of monomer M-4, 0.5 g of 2-methylresorcinol and 0.71 g of 35% formalin were dissolved in 3 ml of ethanol, followed by the addition of 2 drops of hydrochloric acid. The solution was kept heated at reflux temperature for 12 hr to thereby accomplish an addition-condensation reaction. After that the reaction liquid was poured into a large volume of water to precipitate a polymer powder, which had a pale yellow color. This polymer was a novolak resin soluble in various organic solvents such as alcohols, acetone, chloroform and ethyl cellosolve acetate and also in aqueous alkaline solutions such as 1N aqueous solution of sodium hydroxide and 1N aqueous solution of tetramethylammonium hydroxide. This novolak resin is named P-9.

Using the same monomer M-4, another novolak resin P-10 was prepared by varying the quantities of 2-methylresorcinol and 35% formalin in the above described process to 1.0 g and 1.1 g, respectively. Furthermore, several different novolak resins were prepared by differently varying the quantity of 2-methylresorcinol within the range from 0.2 to 2.0 g and the quantity of 35% formalin within the range from 0.5 to 1.7 g, while the quantity of monomer M-4 was invariably 1.0 g. The obtained novolak resins including P-10 were soluble in the above-named organic solvents and aqueous alkaline solutions.

EXAMPLE 6

Five kinds of resist material solutions, RS-8, RS-9, RS-10, RS-11 and RS-12, were prepared by dissolving novolak resin P-9 or P-10 and a photosensitive material, which was selected from Q-1 and Q-3 described in Example 4, in ethyl cellosolve acetate (EEA). The particulars of these solutions are shown in Table 3.

TABLE 3

| Resist Material Solution | Novolak Resin | Photosensitive Material | Solvent |
|---|---|---|---|
| RS-8 | P-9 1.0 g | Q-1 0.2 g | EEA 9 g |
| RS-9 | P-9 1.0 g | Q-3 0.2 g | EEA 9 g |
| RS-10 | P-9 1.0 g | Q-3 0.3 g | EEA 10 g |
| RS-11 | P-10 1.0 g | Q-1 0.2 g | EEA 9 g |
| RS-12 | P-10 1.0 g | Q-3 0.2 g | EEA 9 g |

Resistivity of novolak resin films formed by respectively using the resist material solutions RS-9 and RS-11 to dry etching was evaluated by the following experiment.

The solution RS-9 was applied by spinning to a silicon substrate and dried at 80° C. for 30 min to thereby form a resist film 3600 Angstrom thick. The resist film was subjected to reactive oxygen ion etching. The etching operation conditions: oxygen flow rate was 5 sccm; oxygen pressure was 1.5 Pa; rf power was 50 W. In 10 min, the film thickness decreased from the initial value of 3600 Angstrom to 2900 Angstrom. By the same etching method and under the same etching conditions, a film of the conventional novolak resin MP-1300 was etched by about 12500 Angstrom in 10 min. Therefore, it was understood that a resist film formed by applying the solution RS-9 can be used as a mask for etching a thick organic layer by a reactive oxygen ion etching method.

By the same etching method and under the same etching operation conditions, a film formed by applying the resist material solution RS-11 was etched by 1000 Angstrom in 10 min. Accordingly, a resist film formed by applying RS-11 too can be used as a mask for etching a thick organic layer by a reactive oxygen ion etching method.

In another experiment, a positive resist image produced by optical exposure in a film formed by using RS-9 was transferred into an underlying thick organic layer. First, MP-1300 was spun to a silicon substrate to a thickness of 10000 Angstrom and prebaked at 250° C. for 1 hr. Then the resist material solution RS-9 was spun onto the surface of the prebaked MP-1300 layer and dried at 80° C. for 30 min to thereby form a resist film 2000 Angstrom thick. A positive resist image was produced with submicron linewidth by the steps of placing a patterned chromium mask on the resist film, exposing the masked sample to light for 20 sec by using Kasper 2001P exposure apparatus equipped with a light source of about 4000 Angstrom wavelengths and making development with 0.5N aqueous solution of sodium hydroxide. After rinsing and drying, the MP-1300 layer beneath the resist image was etched by a reactive oxygen ion etching method for 11 min under the etching operation conditions described in the preceding experiment. As the result, the submicron resist image was transferred into the underlying MP-1300 layer with good precision. In an additional run of this experiment, an oxygen ion beam etching method was employed instead of the reactive oxygen ion etching method. Also in this case the transfer of the positive resist image into the underlying MP-1300 layer was achieved with good precision. Furthermore, the resist material solutions RS-8, RS-10, RS-11 and RS-12 were tested in the same manner and gave nearly the same good results.

EXAMPLE 7

Using the materials shown in Table 4, four kinds of novolak resins according to the invention were prepared by the addition-condensation reaction process described in Example 1.

TABLE

| | Raw Materials | | | |
|---|---|---|---|---|
| Novolak Resin | Si—containing phenol (g) | 2-methyl-resorcinol (g) | 35% formalin (g) | Yield of Resin (g) |
| P-11 | M-1 5.0 | 2.1 | 3.6 | 7.6 |
| P-12 | M-2 5.0 | 2.0 | 3.4 | 7.5 |
| P-13 | M-3 5.0 | 5.0 | 5.4 | 10.8 |
| P-14 | M-4 5.0 | 3.0 | 3.9 | 8.5 |

A resist material solution RS-13 was prepared by dissolving 5.0 g of novolak resin P-11, 2.0 g of 2,2-dimethyl-5-diazo-1,3-dioxane-4,6-dione, which was employed as a photosensitive material and will be referred to as Q-4, in 4.5 g of diethyleneglycol dimethyl ether, followed by filtration with a 0.2 micrometers filter. By the same method, additional seven kinds of resist material solutions were prepared by selectively using the novolak resins P-11–P-14 in combination with the photosensitive material Q-4 or another photosensitive material Q-5, which is 2-methyl-2-phenyl-5-diazo-1,3-dioxane-4,6-dione, as shown in Table 5. In every case the solvent was diethyleneglycol dimethyl ether.

TABLE 5

| Resist Material Solution | Novolak Resin | Photosensitive Material | Solvent |
|---|---|---|---|
| RS-13 | P-11 5 g | Q-4 2 g | 45 g |
| RS-14 | P-11 4 g | Q-5 1.8 g | 40 g |
| RS-15 | P-12 5 g | Q-4 2 g | 45 g |
| RS-16 | P-12 5 g | Q-5 2 g | 40 g |
| RS-17 | P-13 5 g | Q-4 1.7 g | 40 g |
| RS-18 | P-13 6 g | Q-5 3 g | 48 g |
| RS-19 | P-14 5 g | Q-4 3 g | 40 g |
| RS-20 | P-14 4 g | Q-5 1.2 g | 40 g |

Using the resist material solution RS-15, an experiment was conducted to form a resist pattern of submicron linewidth by a deep UV exposure method. First, a polyimide resin (PI-2555 of DuPont Co.) was applied by spinning to a silicon substrate and prebaked at 350° C. for 1 hr to thereby form a 1.3 micrometers thick layer of PI-2555. Next, the resist material solution RS-15 was spun onto the surface of the prebaked PI-2555 layer and dried at 80° C. for 30 min to thereby form a resist film 2800 Angstrom thick. A fine positive pattern of 0.5 micrometers linewidth was formed in the resist film with a patterned chromium mask placed thereon by deep UV exposure using a light source of 254 nm wavelength. The dose was 600 mj/cm². Development was performed with 0.15N aqueous solution of sodium hydroxide followed by rinsing with water. After drying, the PI-2555 layer was etched for 10 min by using a reactive oxygen ion etching apparatus of the parallel plate type. The etching operation conditions: rf power density was 0.08 W/cm²; oxygen flow rate was 5 sccm; oxygen pressure was 1.6 Pa. As the result, the submicron positive pattern initially formed in the resist film was transferred into the PI-2555 layer with high precision. This experiment was repeated by alternatively using the other resist material solutions shown in Table 5, and similarly good results were obtained.

EXAMPLE 8

A resist material solution RS-21 was prepared by dissolving 5 g of the novolak resin P-7 prepared in Example 2 and 1.5 g photosensitive material Q-3 in 43.5 g of ethyl cellosolve acetate.

First, the polyimide resin PI-2555 was spun to a silicon substrate and prebaked at 350° C. for 1 hr to thereby form a 13000 Angstrom thick layer of polyimide. Then the resist material solution RS-21 was spun onto the surface of the polyimide layer and dried at 80° C. for 30 min to thereby form a resist film 3000 Angstrom thick. A submircon positive pattern was formed in the resist film with a chromium mask place thereon by exposure to light for 20 sec by using Kasper 2001P exposure apparatus equipped with a light source of 4000 Angstrom wavelength, followed by development with 0.3N aqueous solution of sodium hydroxide. The obtained resist pattern was cured by flood irradiation with xenon-mercury lamp at a dose of 2 J/cm². After that, dry etching of the underlying prebaked PI-2555 layer was carried out by using a reactive oxygen ion etching apparatus of the parallel plate type. As the results, the submicron resist pattern was transferred into the PI-2555 layer with very high precision. More particularly, the linewidth loss accompanying the transfer of the pattern was only 0.05 micrometers on both sides of line. For comparison, when the curing of the resist pattern by exposure to xenon-mercury lamp was omitted in the above patterning process the linewidth loss was 0.15 micrometers. Besides, the curing of the resist pattern resulted in improved rectangularity of the transferred pattern with no indication of sagging during the transferring ething.

The above experiment was repeated by using another resist material solution, which was prepared by using the novolak resin P-9 of Example 5 in place of P-7 in the solution RS-21. Also in this case, curing of the resist pattern by irradiation deep UV light produced similarly good effects on the precision of the pattern transferred into the polyimide layer.

What is claimed is:

1. A novolak resin comprising structural units having a trimethylsilyl group attached to benzene ring of a phenol via at least one methylene group.

2. A novolak resin according to claim 1, wherein said structural units are represented by the general formula (A):

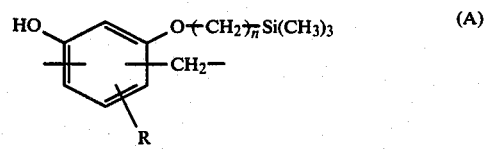

wherein R represents hydrogen atom or an alkyl group, and n is a positive integer.

3. A novolak resin according to claim 2, further comprising second structural units represented by the formula (C):

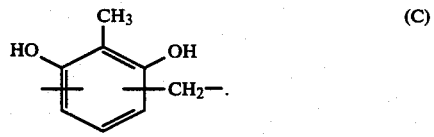

4. A novolak resin according to claim 2, wherein said structural units are represented by the general formula (AA):

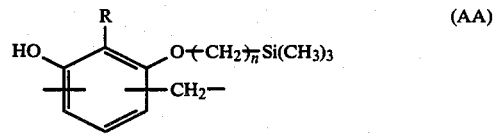

wherein R represents hydrogen atom or methyl group, and n is an integer of 1 to 3.

5. A novolak resin according to claim 2, wherein the degree of polymerization of said structural units is not greater than 20.

6. A novolak resin according to claim 1, wherein said structural units are represented by the general formula (B):

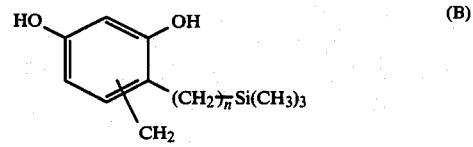

wherein n is a positive integer.

7. A novolak resin according to claim 6, further comprising second structural units represented by the formula (C):

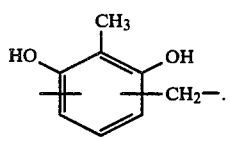

8. A novolak resin according to claim 6, wherein said n in the formula (B) is not larger than 4.

9. A novolak resin according to claim 6, wherein the degree of polymerization of said structural units is not greater than 20.

10. A novolak resin according to claim 1, wherein the content of said structural units in the novolak resin is in the range from 20 to 80% by mol.

11. A resist material comprising a novolak resin, which comprises structural units having a trimethylsilyl group attached to benzene ring of a phenol via at least one methylene group, and a photosensitive diazo compound.

12. A resist material according to claim 11, wherein said structural units are represented by the general formula (A):

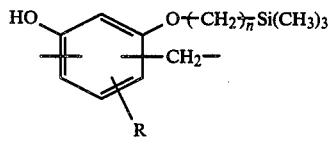

wherein R represents hydrogen atom or an alkyl group, and n is a positive integer.

13. A resist material according to claim 12, wherein said novolak resin further comprises second structural units represented by the formula (C):

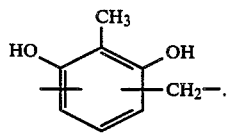

14. A resist material according to claim 12, wherein said structural units are represented by the general formula (AA):

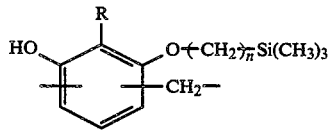

wherein R represents hydrogen atom or methyl group, and n is an integer of 1 to 3.

15. A resist material according to claim 11, wherein said structural units are represented by the general formula (B):

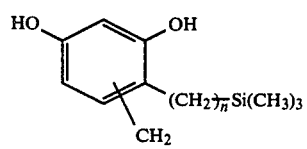

wherein n is a positive integer.

16. A resist material according to claim 15, wherein said novolak resin further comprises second structural units represented by the formula (C):

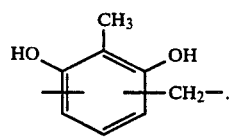

17. A resist material according to claim 15, wherein said n in the formula (B) is not larger than 4.

18. A resist material according to claim 11, wherein the content of said structural units in said novolak resin is in the range from 20 to 80% by mol.

19. A resist material according to claim 11, wherein the proportion of said diazo compound to said novolak resin is in the range from 5:100 to 100:100 by weight.

20. A resist material according to claim 11, wherein said diazo compound is a quinonediazide compound.

21. A resist material according to claim 20, wherein the proportion of said diazo compound to said novolak resin is in the range from 15:100 to 50:100 by weight.

22. A resist material according to claim 11, wherein said diazo compound is representated by general formula (D):

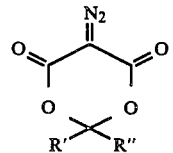

wherein each of R' and R" represents a substituted or unsubstituted alkyl group or a substituted or unsubstituted aryl group, and R' and R" is either identical or different.

23. A resist material according to claim 22, wherein the proportion of said diazo compound to said novolak resin is in the range from 20:100 to 50:100 by weight.

24. A method of forming a pattern in the manufacture of microelectronic devices, the method comprisng the steps of:
  forming an organic polymer layer which can be etched by dry etching on a substrate;
  forming resist film on said organic polymer layer by using a resist material which comprises a novolak resin comprising structural units having a trimethylsilyl group attached to benzene ring of a phenol via at least one methylene group and a photosensitive diazo compound;
  forming a desired pattern in said resist film by a lithography technique; and
  etching said organic polymer layer by a dry etching technique with the patterned resist film as a mask.

25. A method according to claim 24, wherein said structural units are represented by the general formula (A):

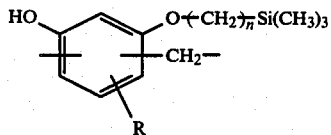

wherein R represents hydrogen atom or an alkyl group, and n is a positive integer.

26. A method according to claim 25, wherein said structural formula is represented by the general formula (AA):

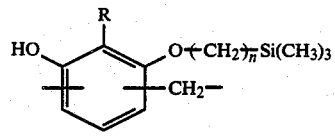

wherein R represents hydrogen atom or methyl group, and n is an integer of 1 to 3.

27. A method according to claim 25, wherein said novolak resin further comprises secondary structural units represented by the formula (C):

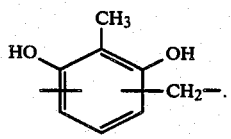

28. A method according to claim 24, wherein said structural units are represente by the general formula (B):

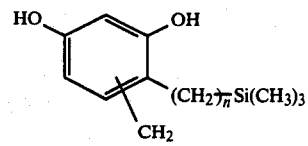

wherein n is a positive integer not larger than 4.

29. A method according to claim 28, wherein said novolak resin further comprises secondary structural units represented by the formula (C):

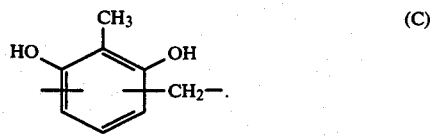

30. A method according to claim 24, wherein said diazo compound is a quinonediazide compound.

31. A method according to claim 24, wherein said diazo compound is represented by the general formula (D):

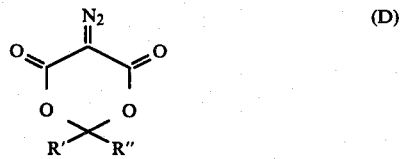

wherein each of R' and R" represents a substituted or unsubstituted alkyl group or a substituted or unsubstituted aryl group, and R' and R" are either identical or different.

32. A method according to claim 24, further comprisng the step of curing the patterned resist film before the step of etching said organic polymer layer by irradiation with deep UV rays.

33. A method according to claim 24, wherein said lithography technique is an optical lithography technique.

34. A method according to claim 24, wherein said lithography technique uses an aqueous solution of an alkaline compound as a developer liquid to develop the pattern delineated in said resist film.

* * * * *